(12) United States Patent
Watanabe et al.

(10) Patent No.: US 9,885,675 B2
(45) Date of Patent: Feb. 6, 2018

(54) IONIZING RADIATION DETECTION APPARATUS

(71) Applicant: CANON KABUSHIKI KAISHA, Tokyo (JP)

(72) Inventors: Ikuo Watanabe, Yokohama (JP); Kazuyoshi Ishii, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 81 days.

(21) Appl. No.: 15/157,203

(22) Filed: May 17, 2016

(65) Prior Publication Data

US 2016/0341676 A1    Nov. 24, 2016

(30) Foreign Application Priority Data

May 20, 2015  (JP) .................................. 2015-102820

(51) Int. Cl.
*G01N 23/20*    (2006.01)

(52) U.S. Cl.
CPC . *G01N 23/20066* (2013.01); *G01N 2223/638* (2013.01)

(58) Field of Classification Search
CPC ....... G01N 23/20066; G01N 2223/638; H04N 5/32; A61B 6/4233; A61B 6/4241; G01T 1/2928; G01T 1/2935
See application file for complete search history.

(56) References Cited

U.S. PATENT DOCUMENTS

2008/0128631 A1* 6/2008 Suhami .................... G01T 5/02
250/370.09

2009/0084972 A1* 4/2009 Tamagawa ................ G01T 1/18
250/374
2015/0115992 A1* 4/2015 Fushie .................. H01J 43/246
324/759.01

FOREIGN PATENT DOCUMENTS

JP    2001-13251 A     1/2001
JP    2010-078319 A    4/2010

OTHER PUBLICATIONS

Shigeto Kabuki, et al, Imaging Study of a Phantom and Small Animal with a Two-Head Electron-Tracking Compton Gamma-Ray Camera, 2010 IEEE, 2844-2847.

* cited by examiner

*Primary Examiner* — David Porta
*Assistant Examiner* — Mindy Vu
(74) *Attorney, Agent, or Firm* — Canon U.S.A., Inc. IP Division

(57) ABSTRACT

An ionizing radiation detection apparatus of the present disclosure includes a first drift electrode disposed inside a chamber and a first detection unit disposed inside the chamber so as to oppose the first drift electrode, wherein the first detection unit is configured to detect a first ionization electron produced through Compton scattering caused by an incident γ-ray inside the scattering gas, and a second drift electrode configured to emit a reference X-ray upon being excited by the incident γ-ray with a second detection unit disposed so as to oppose the second drift electrode and configured to detect a second ionization electron produced as the reference X-ray is photoelectrically absorbed by the scattering gas, and a control unit configured to compensate for a change in an amplification factor of a signal output from each of the first detection unit and the second detection unit.

8 Claims, 8 Drawing Sheets

IONIZING RADIATION DETECTION APPARATUS

BACKGROUND

Field of the Disclosure

The present disclosure relates to ionizing radiation detection apparatuses of an electron tracking type.

Description of the Related Art

An advanced Compton method is known as a conventional method for detecting a γ-ray. In the stated method, the incident direction of an incident γ-ray is calculated with the use of the energy and the scattered direction vector of a scattered γ-ray produced through Compton scattering as well as the energy and the recoil direction vector of a recoil electron produced through the Compton scattering.

Nuclear Science Symposium Conference Record (NSS/MIC 2010) discloses a time projection chamber (TPC), which is a γ-ray detection apparatus that utilizes an advanced Compton method. The TPC is filled with a gas serving as a scatterer, and a planar electron collector (μ-PIC) that multiplies an ionization electron and detects multiplied ionization electrons is disposed inside the TPC. A recoil electron produced through Compton scattering travels while successively ionizing gas molecules and produces an electron cloud formed of a number of ionization electrons in its trajectory. This electron cloud is subjected to the force of an electric field in an electron drift region and drifts to the electron collector while retaining substantially the same shape as the trajectory of the recoil electron. The electron collector carries out gas electron multiplication through an electron avalanche effect and detects the projection position of the electron cloud (trajectory) on a two-dimensional plane.

Japanese Patent Laid-Open No. 2010-078319 discloses a radiation gas monitor that corrects a gain variation arising in part from a deterioration over time of a scintillator in a radiation detector.

A secondary electron ionized by a recoil electron is multiplied by a gas electron multiplier, but the gas electron multiplication factor varies as an outgassed substance from an inner surface or an internal structure of the gas chamber is mixed thereinto or as a quencher gas decomposes and deteriorates. Accordingly, the accuracy in determining the position (direction) of an incident γ-ray calculated on the basis of the detected energy of the recoil electron is reduced.

The energy of a calibration radiation source used in Japanese Patent Laid-Open No. 2010-078319 is higher than the energy of the source for measurement radiation. When the calibration radiation source emits a β-ray, a low-energy secondary electron can be mixed into a measurement energy region and detected as noise; and when the calibration radiation source emits a γ-ray, a low-energy scattered γ-ray produced through Compton scattering or a low-energy secondary electron can be mixed into the measurement energy region and detected as noise.

SUMMARY OF THE DISCLOSURE

The present disclosure provides an ionizing radiation detection apparatus that includes a chamber holding a scattering gas thereinside; a first drift electrode disposed inside the chamber; a first detection unit disposed inside the chamber so as to oppose the first drift electrode, the first detection unit being configured to detect a first ionization electron produced through Compton scattering caused by an incident γ-ray inside the scattering gas; a second drift electrode configured to emit a reference X-ray upon being excited by the incident γ-ray; a second detection unit disposed so as to oppose the second drift electrode, the second detection unit being configured to detect a second ionization electron produced as the reference X-ray is photoelectrically absorbed by the scattering gas; and a control unit configured to compensate for a change in an amplification factor of a signal output from each of the first detection unit and the second detection unit.

Further features of the present disclosure will become apparent from the following description of exemplary embodiments with reference to the attached drawings.

DESCRIPTION OF THE EMBODIMENTS

Hereinafter, exemplary embodiments of the present disclosure will be described with reference to the drawings.

First Exemplary Embodiment

Figure 1:
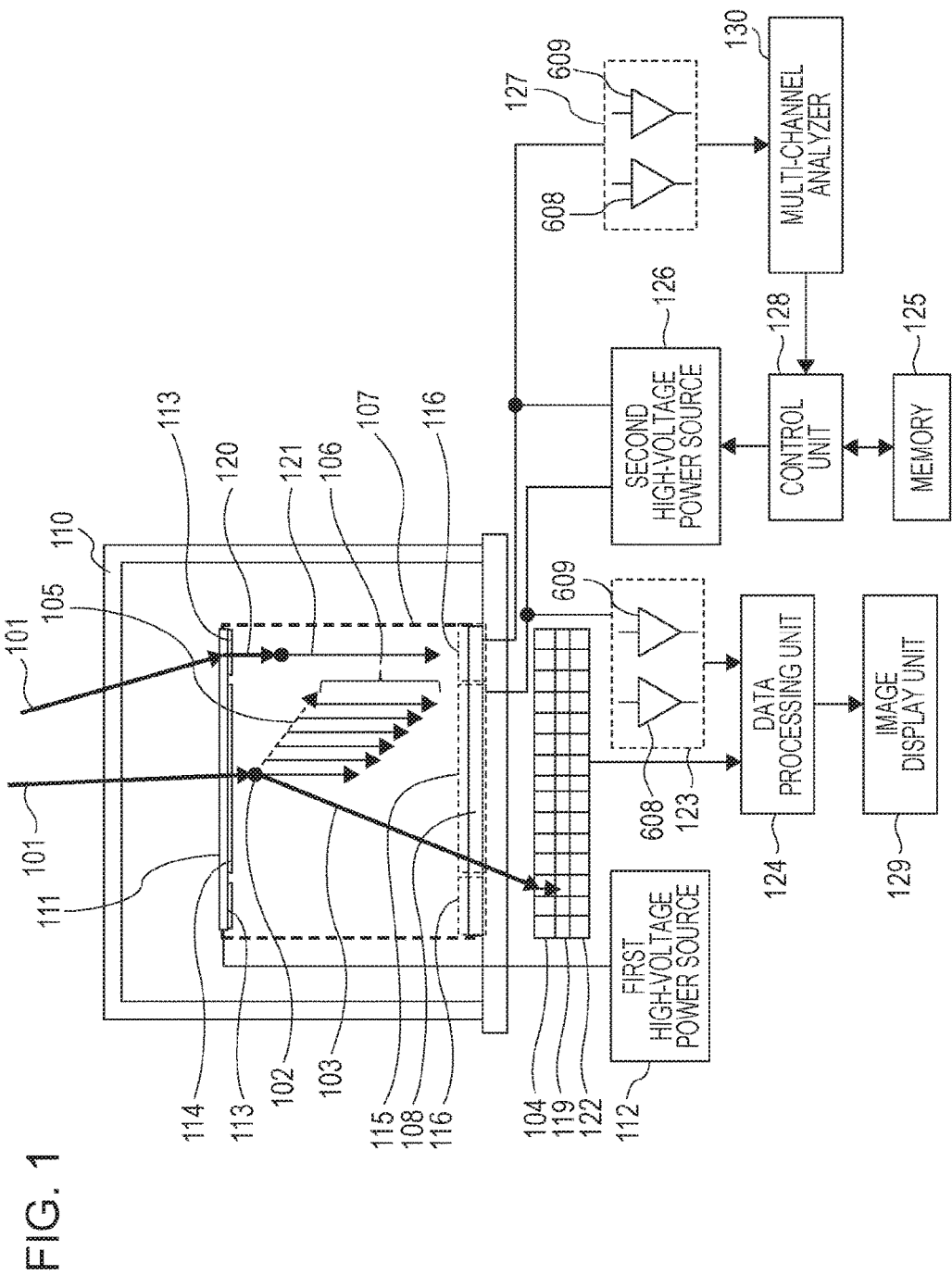
FIG. 1 illustrates a configuration of an ionizing radiation detection apparatus according to an exemplary embodiment of the present disclosure.

As illustrated in FIG. 1, a chamber 110 is filled with a scattering gas 102 (e.g., Ar+10% methane or ethane) for detecting ionizing radiation, and a drift cage 107 is disposed inside the chamber 110. A drift plane 111 and a fluorescent X-ray generation plate 113 are disposed at an upper portion of the drift cage 107. A secondary electron detection unit 108, which is an electron sensor, is provided inside the chamber 110 at a lower portion thereof.

Figure 7:
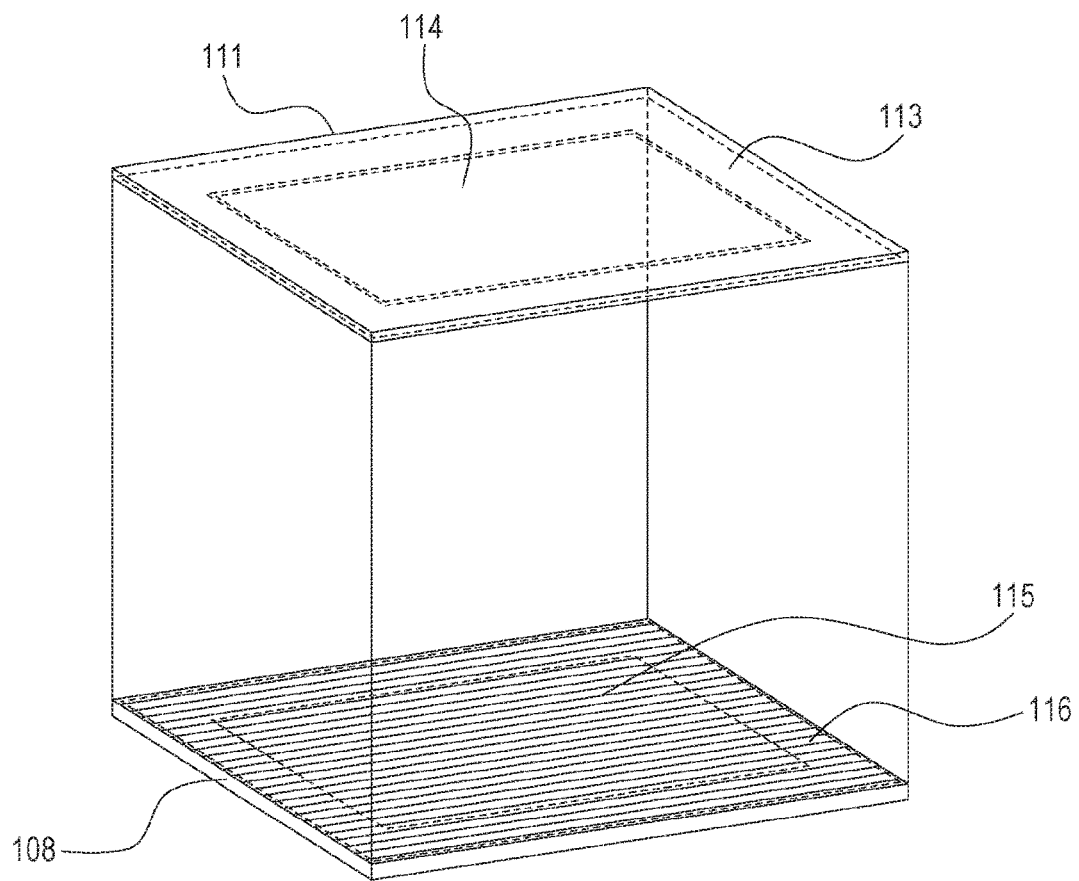
FIG. 7 is a perspective view of a drift cage according to an exemplary embodiment of the present disclosure.

As illustrated in FIG. 7, a first drift electrode 114, which is constituted by an aluminum thin film, is disposed on a lower surface of the drift plane 111, which opposes the secondary electron detection unit 108. In addition, the fluorescent X-ray generation plate 113, which is constituted by a copper thin film, is disposed on the lower surface of the drift plane 111 at a portion surrounding the first drift electrode 114. The fluorescent X-ray generation plate 113 emits a reference X-ray 120 upon being excited by an incident γ-ray. The fluorescent X-ray generation plate 113 also serves as a second drift electrode for generating a drift electric field. A negative high voltage is applied to the first drift electrode 114 and the second drift electrode (fluorescent X-ray generation plate) 113 by a first high-voltage power source 112, and thus a drift electric field is generated between the first drift electrode 114 and the secondary electron detection unit 108 and between the second drift electrode 113 and the secondary electron detection unit 108.

With reference to FIG. 1, an operation of the ionizing radiation detection apparatus will now be described. An incident γ-ray 101 passes through the chamber 110 and the drift plane 111 and causes Compton scattering to occur in the scattering gas 102. This Compton scattering produces a scattered γ-ray 103 and recoil electrons 105, and the recoil electrons 105 produce secondary electrons 106 (first ionization electrons). The scattered γ-ray 103 is converted to scintillation light by a scintillator 104 of a two-dimensional array. The scintillation light is photoelectrically converted and multiplied by a multi-anode photomultiplier tube (MAPMT) 119 and is then converted to an electric signal by a head amplifier array 122 disposed underneath the MAPMT 119. The electric signal is sent to a data processing unit 124 as information on the sensed position of the scattered γ-ray 103 and the energy of the scattered γ-ray 103.

On the basis of an output of the secondary electron detection unit 108 and an output of a γ-ray detection unit constituted by the scintillator 104 and the MAPMT 119, the intensity distribution of the incident γ-ray 101 can be turned into an image, and the image can be displayed on an image display unit 129.

In the meantime, the secondary electron detection unit 108 is divided into a first detection unit 115, which opposes the first drift electrode 114, and a second detection unit 116, which opposes the second drift electrode. The secondary electrons 106 move to the secondary electron detection unit 108 along the drift electric field and are detected by the first detection unit 115. An output of the first detection unit 115 is amplified by a measurement amplifier (first amplification unit) 123, and the amplified output is sent to the data processing unit 124. The data processing unit 124 carries out an inverse calculation of the Compton scattering on the basis of the positional information and the energy information of the scattered γ-ray 103 and the trajectory vector information and the energy information of the recoil electrons 105, and the direction in which the incident γ-ray 101 has entered is calculated. The result of the calculation of the direction in which the incident γ-ray 101 has entered is displayed on the image display unit 129 in the form of an image. Meanwhile, an output of the second detection unit 116 is used to control the gain (amplification factor) in the process of obtaining the energy information from the secondary electrons 106 detected by the first detection unit 115.

Figure 6:
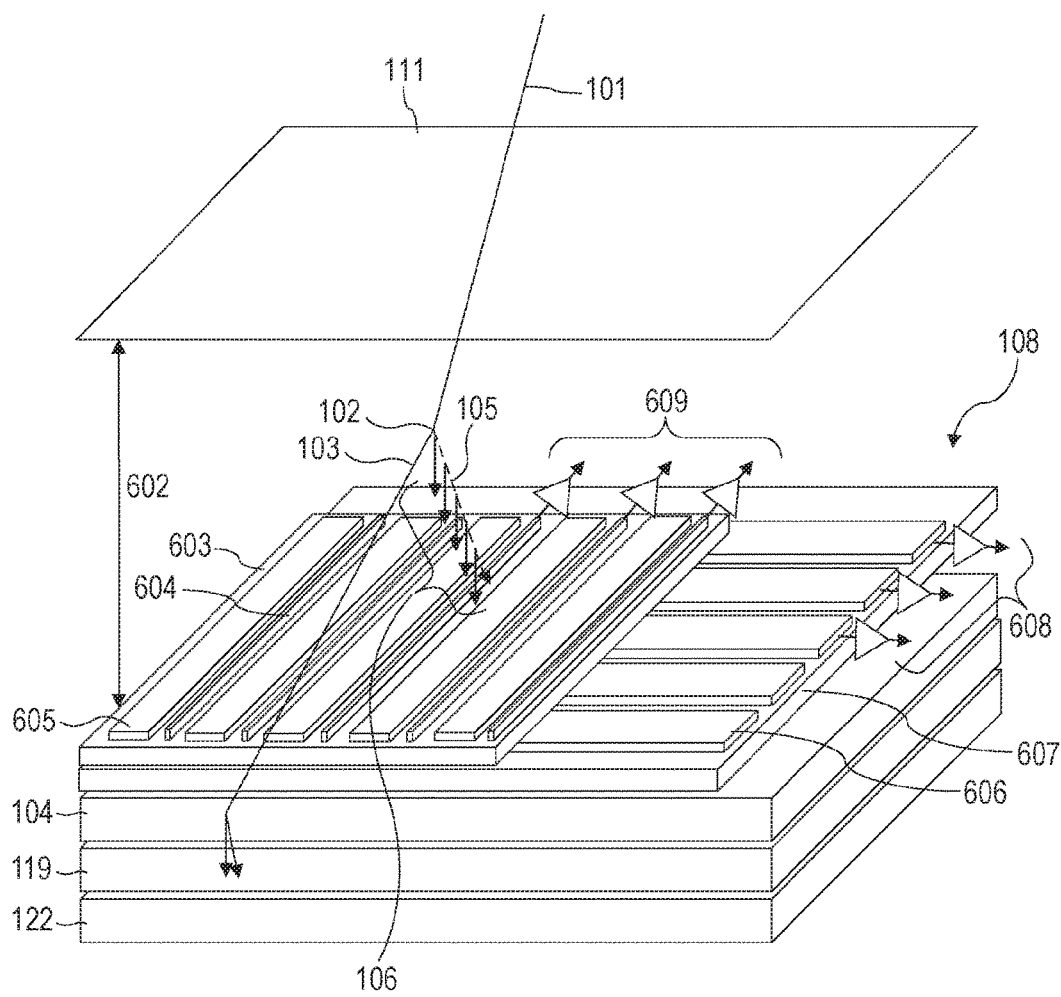
FIG. 6 is a schematic diagram for describing a microstrip gas chamber (MSGC), in accordance with one or more exemplary embodiments of the present disclosure.

FIG. 6 illustrates a configuration of a microstrip gas chamber (MSGC), serving as an example of the secondary electron detection unit 108. The secondary electrons 106 produced from the recoil electrons 105 reach the secondary electron detection unit 108 through the drift electric field. Anode strips 604 and cathode strips 605 are provided on an upper surface (detection surface) of the secondary electron detection unit 108. An electric field of 100,000 V/cm or higher is being applied between the anode strips 604 and the cathode strips 605 by a second high-voltage power source 126 (the intervals between the anode strips 604 and the cathode strips 605 are approximately 50 μm, and thus an actual potential difference is approximately 500 V). The secondary electrons 106 move toward the anode strips 604 having a higher potential but are subjected to the gas electron multiplication through the electron avalanche effect immediately prior to reaching the anode strips 604, and more secondary electrons 106 are produced. The gas electron multiplication factor in this process is approximately several ten thousand. The multiplied secondary electrons 106 are amplified and read out by anode amplifiers 609, which makes it possible to determine which anode strips 604 the secondary electrons 106 have reached.

Back strips 606 are disposed underneath the anode strips 604 so as to extend perpendicularly to the anode strips 604 with a substrate 603, serving as an insulation layer, interposed therebetween. Induced currents generated by the secondary electrons 106 that have reached the anode strips 604 are amplified by back strip amplifiers 608 and the amplified induced currents are output. As the anode strips 604 and the back strips 606 that the secondary electrons 106 have reached are identified, the positions at which the secondary electrons 106 have reached within the detection surface can be identified by the intersections.

The anode amplifiers 609 connected to the anode strips 604 included in the first detection unit 115 (see FIG. 7) and the back strip amplifiers 608 connected to the back strips 606 constitute the measurement amplifier 123. The amplification factor of the measurement amplifier 123 is approximately 1000×. The second detection unit 116 has a configuration similar to that of the first detection unit 115. The anode amplifiers 609 connected to the anode strips 604 included in the second detection unit 116 and the back strip amplifiers 608 connected to the back strips 606 constitute a calibration amplifier (second amplification unit) 127. It is to be noted that, although only five anode strips 604 are depicted schematically in FIG. 6, in reality, approximately 200 anode strips 604 are disposed and each anode strip 604 has a width of approximately 200 μm. Each cathode strip 605 has a width of approximately 100 μm. Each back strip 606 has a width of approximately 200 μm.

Figure 2:
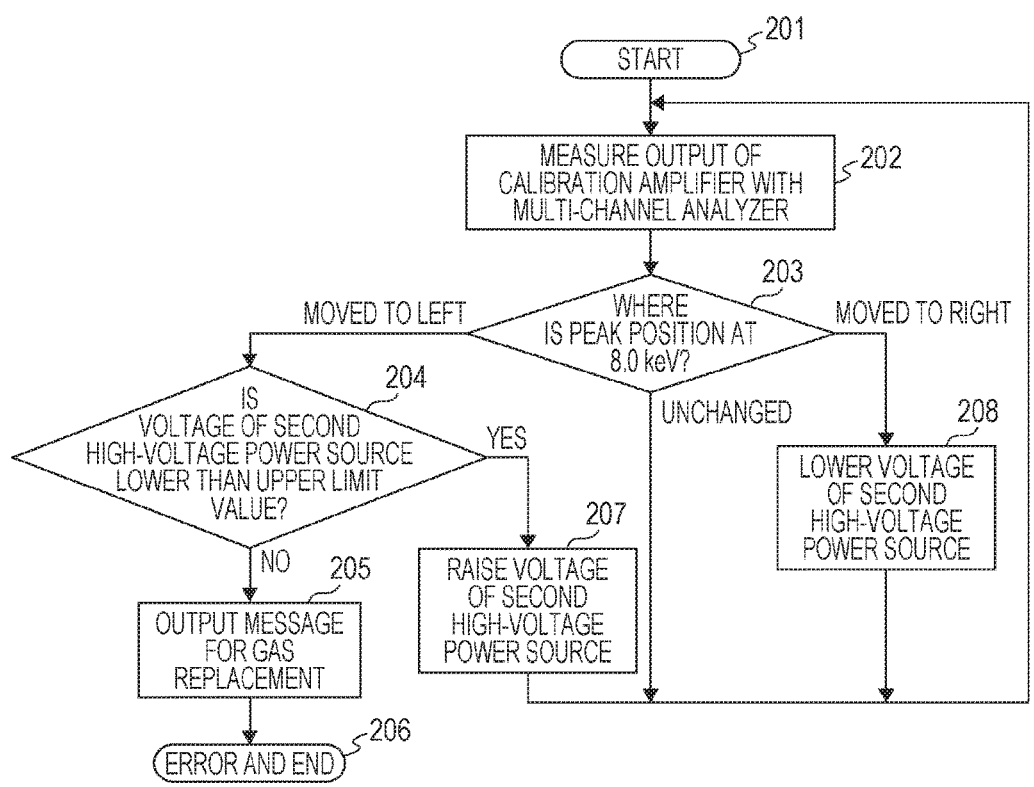
FIG. 2 is a flowchart for describing an operation of the ionizing radiation detection apparatus according to an exemplary embodiment of the present disclosure.

With reference to FIG. 2, a method of controlling the gain (amplification factor) in the process of calculating the energy of recoil electrons from signals of the secondary electrons 106 detected by the first detection unit 115 will now be described. Some of the incident γ-rays 101 pass through the chamber 110 and strike the fluorescent X-ray generation plate 113. Copper atoms constituting the fluorescent X-ray generation plate 113 are excited by this incident γ-ray and emit a reference X-ray 120 (K-line) having an energy of 8.0 keV. The reference X-ray 120 is photoelectrically absorbed by the scattering gas 102 at high probability to produce an ionization electron. At this time, the substantially entire energy of the reference X-ray 120 is absorbed, and the ionization electron thus has an energy of 8.0 keV. Furthermore, this ionization electron is scattered a plurality of times by molecules contained in the scattering gas 102, and a number of secondary electrons 121 (second ionization electrons) are produced. Most of the secondary electrons 121 are produced between the second drift electrode 113 and the second detection unit 116 and move to the secondary electron detection unit 108 through the drift electric field. An output from the second detection unit 116 obtained on the basis of the secondary electrons 121 that have reached the secondary electron detection unit 108 is sent to a multi-channel analyzer 130 via the calibration amplifier 127.

Figure 5:
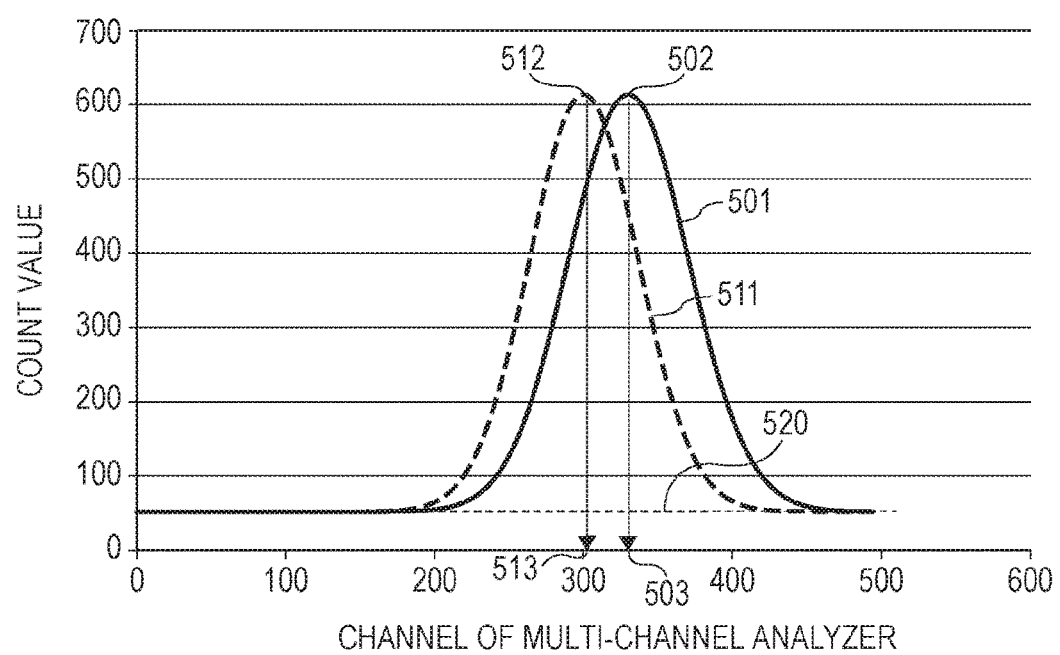
FIG. 5 is a graph illustrating a relation between the energy of a reference X-ray and a count value, in accordance with one or more exemplary embodiments of the present disclosure.

After the operation starts (step 201), an output of the calibration amplifier 127 is measured with the multi-channel analyzer 130 (step 202), and a peak position at 8.0 keV corresponding to the reference X-ray 120 is measured from the waveform (step 203). With reference to FIG. 5, the observation characteristics of the energy of the reference X-ray 120 will now be described. In FIG. 5, the horizontal axis represents the energy, and the vertical axis represents the count value of the incident radiation. An output of the multi-channel analyzer 130 held when shipped after being manufactured or after the scattering gas 102 has been replaced is indicated by a solid line 501. A value 503 of the energy at the peak 502 of the count value at this time is written into a memory 125 as an initial value. When the gas serving as a scatterer deteriorates, the gas electron multiplication factor in the secondary electron detection unit 108 decreases, and the overall energy changes and shifts to the left even when the count value remains the same, as indicated by a dashed line 512. A control unit 128 controls the set voltage of the second high-voltage power source 126 (the potential to be applied to the secondary electron detection unit 108) in accordance with an energy value 513 measured by the multi-channel analyzer 130. When the peak position has moved to the left, it is determined whether the set voltage of the second high-voltage power source 126 is lower than a prescribed upper limit value (step 204). If the set voltage is lower than the upper limit value, the second high-voltage power source 126 is stepped up so that the energy value 513 at the peak of the count value of the output of the multi-channel analyzer 130 takes the initial value written in the memory 125 (step 207). In other words, the gas electron multiplication factor of the secondary electron detection unit 108 is raised. When the set voltage of the second high-voltage power source 126 is no lower than the prescribed upper limit value, it is determined that it is time to replace the gas due to the deterioration of the gas. Thus, a message urging a gas replacement is output (step 205), and the processing is terminated for an error (step 206).

An equal voltage is being applied to the first detection unit 115 and the second detection unit 116 by the second high-voltage power source 126, and thus the first detection unit 115 that detects the secondary electrons 106 is controlled to have a constant gas electron multiplication factor along with the gas electron multiplication factor of the second detection unit 116. Consequently, a change in the total gain across the entire process of calculating the energy of the recoil electrons 105 from the secondary electrons 106 is compensated for, and the total gain can be kept constant over time. It is to be noted that a background noise level 520 indicated in FIG. 5 corresponds to the level of noise caused by radiation radiated from an environment or electric systems and a case in which the background noise level 520 is around 50 counts is indicated.

A fluorescent X-ray generation material constituting the fluorescent X-ray generation plate 113 will now be described. A fluorescent X-ray is generated through an energy difference arising when an inner-shell electron of a constituent atom is excited by γ-ray irradiation and an outer-shell electron makes a transition to a hole produced in the inner shell. A fluorescent X-ray is used to calibrate the energy of a secondary electron 106 detected by the secondary electron detection unit 108, utilizing a property that the energy of the fluorescent X-ray is constant and is equal to the energy difference between the inner shell and the outer shell. It is desirable that the energy of a fluorescent X-ray to be used to calibrate the energy fall within an energy range to be calibrated and that the energy width be narrow. Accordingly, it is desirable that the energy level of an excitation electron be in the K shell. A reason for this is that shells other than the K shell have a plurality of orbits and thus there are a plurality of energy levels to which an electron makes a transition. When high-energy electrons in the outer shell make a transition to a plurality of energy levels, fluorescent X-rays having a plurality of energies within a narrow range are emitted. Thus, these fluorescent X-rays cannot be separated, and the energy width thereof is broadened. For example, when a hole is created in the K shell, the F shell has a single energy level, and the energy levels of electrons that make a transition to the K shell are two energy levels ($K_{\alpha 1}$-line and $K_{\alpha 2}$-line) from the L shell and an energy level ($K_\beta$-line) from the M shell. These result in primary fluorescent X-rays. In contrast, when a hole is created in the L shell, the L shell to which an electron makes a transition has two levels, the M shell from which an electron makes a transition has three levels, and the N shell has four levels. Thus, fluorescent X-rays having a number of energies are produced, and such fluorescent X-rays cannot be separated. Therefore, the energy width of the fluorescent X-rays appears as if it is broadened. For the reasons described above, it is desirable that the fluorescent X-ray to be used for calibration be the K-line. Furthermore, it is desirable that the L-line that has an energy contained in the energy region to be calibrated be not produced. A fluorescent X-ray generation material that satisfies the above conditions is selected.

Figure 8:
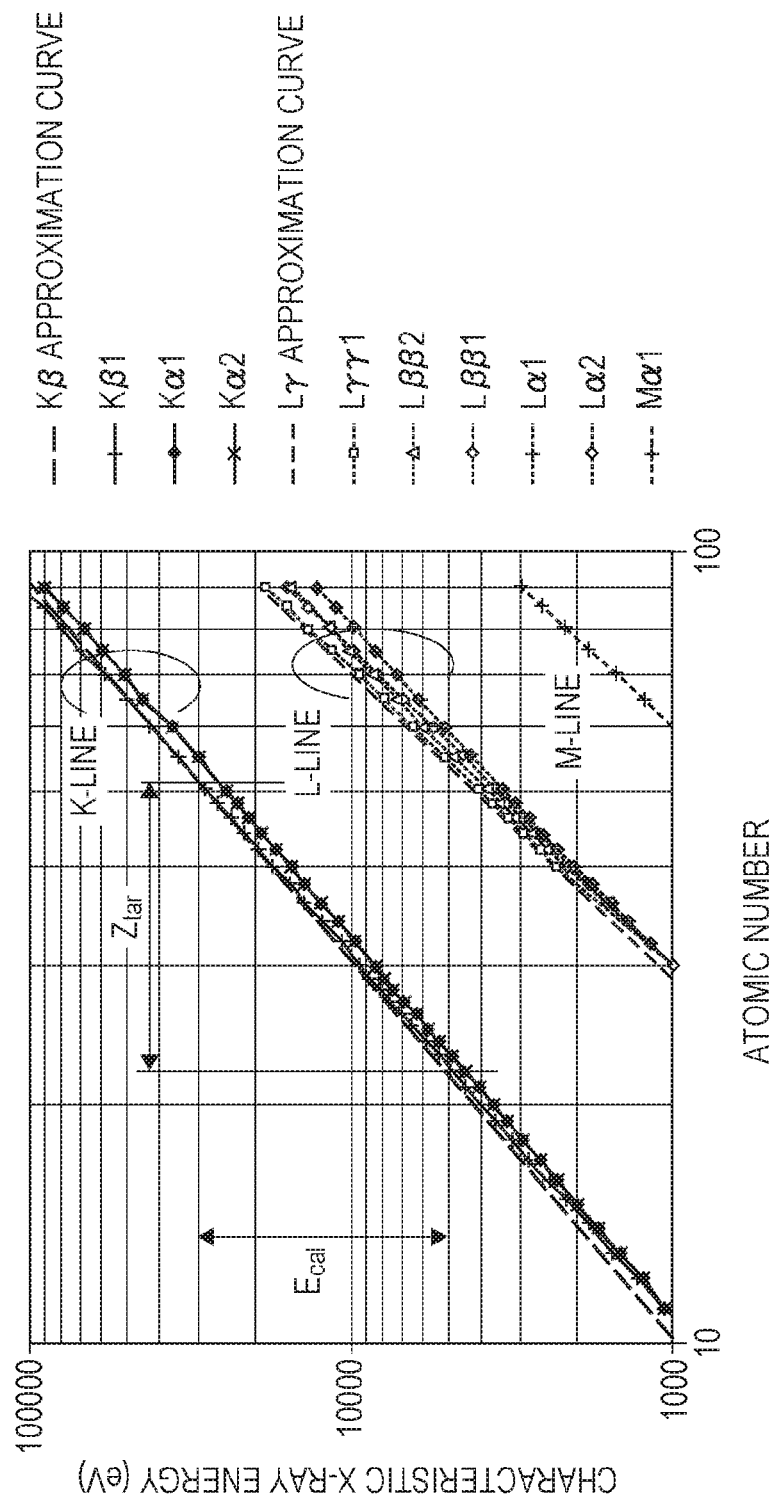
FIG. 8 is a graph illustrating a relation between an atomic number of an element and the energy of a generated fluorescent X-ray, in accordance with one or more exemplary embodiments of the present disclosure.

FIG. 8 illustrates a relation between an atomic number of an element and the energy of a generated fluorescent X-ray. A $K_{\alpha 1}$-line a $K_{\alpha 2}$-line, and a $K_\beta$-line are indicated for the K-line; primary lines are indicated for the L-line; and an $M_{\alpha 1}$-line is indicated for the M-line. When the energy of the $K_\beta$-line is represented by $E_K$ and the energy of the $L_\gamma$-line is represented by $E_L$ (the unit is eV), $E_K$ and $E_L$ are expressed through the following approximation formulas (1) and (2). FIG. 8 also illustrates the calculated values (approximation curves) obtained through these expressions.

$$E_K = 7.7 \times Z^{2.1} \tag{1}$$

$$E_L = 0.16 \times Z^{2.6} \tag{2}$$

Here, the range of the energy $E_{cal}$ to be used for calibration as the reference X-ray 120 is set to be no less than $E_1$ and no greater than $E_2$, the following expression (3) is obtained from the condition of the K-line, and the expression (4) is obtained from the condition of the L-line.

$$E_1 \leq 7.7 \times Z^{2.1} \leq E_2 \tag{3}$$

$$0.16 \times Z^{2.6} \leq E_1 \tag{4}$$

Thus, on the basis of the above expressions (3) and (4), an element for constituting the fluorescent X-ray generation material can be selected. For example, when $E_1$ is 5 keV and $E_2$ is 30 keV, the expression (3) yields the condition that the range of the atomic number Z is from 22 to 51, and the expression (4) yields the condition that the atomic number Z is no greater than 53. The range that simultaneously satisfies these conditions (Z is no less than 22 and no greater than 51) is indicated by $Z_{tar}$. An element for constituting the fluorescent X-ray generation material can be selected on the basis of this result. For example, when copper (Z=29) is used, the energy of the K-line to be generated is 8.0 keV, which satisfies the condition for the reference X-ray 120, and the energy of the L-line to be generated is 0.95 keV, which also satisfies the condition. In addition, when molybdenum (Z=42) is used, the energy of the K-line to be generated is 19.6 keV, which satisfies the condition for the reference X-ray 120, and the energy of the L-line to be generated is 2.6 keV, which also satisfies the condition. Furthermore, both materials are electrically conductive and are thus suitably used to serve as the second drift electrode 113 as well.

Meanwhile, a fluorescent X-ray generated from the first drift electrode 114 can be detected as noise when detecting the secondary electrons 106. To prevent such a situation, it is desirable that the energy of the fluorescent X-ray (K-line) to be generated be no greater than $E_1$, or in other words, the following expression (5) be satisfied.

$$7.7 \times Z^{2.1} \leq E_1 \tag{5}$$

Thus, on the basis of the expression (5), an element for constituting the first drift electrode 114 is selected.

For example, when $E_1$ is 5 keV, the expression (5) yields that the range of the atomic number Z is no greater than 21. For example, when aluminum (Z=13) is used, the energy of the K-line to be generated is 1.5 keV, which satisfies the above condition. Aside from aluminum, beryllium (Z=4), carbon (Z=6), magnesium (Z=12), or the like also satisfies the above condition. In other words, an element having an atomic number of no less than 4 and no greater than 21 is suitable.

Second Exemplary Embodiment

Figure 3:
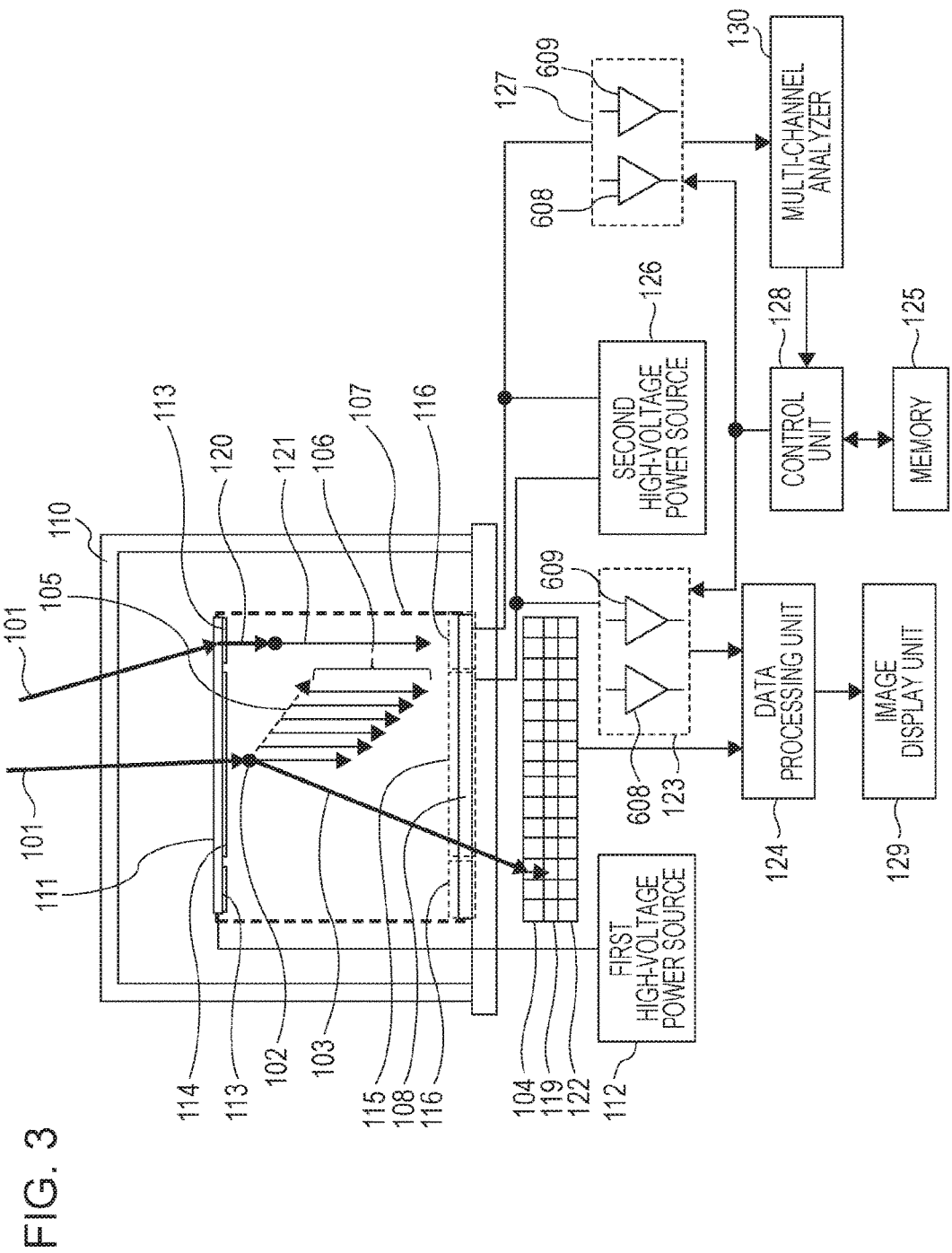
FIG. 3 illustrates a configuration of an ionizing radiation detection apparatus according to an exemplary embodiment of the present disclosure.

As illustrated in FIG. 3, in the present exemplary embodiment, the amplification factors (electrical amplification gains) of the measurement amplifier 123 and the calibration amplifier 127 are controlled through an output of the control unit 128 instead of by controlling the voltage of the second high-voltage power source 126. Circuit of the same characteristics are used for the measurement amplifier 123 and the calibration amplifier 127, and the same gain control values are set therein. As a gain control value that is identical to the gain control value of the calibration amplifier 127 is applied to the measurement amplifier 123, the gain of the measurement amplifier 123 is corrected in a similar manner. In other words, the total gain across the entire process of calculating the energy of the recoil electrons 105 from the generation of the secondary electrons 106 can be kept constant over time.

Figure 4:
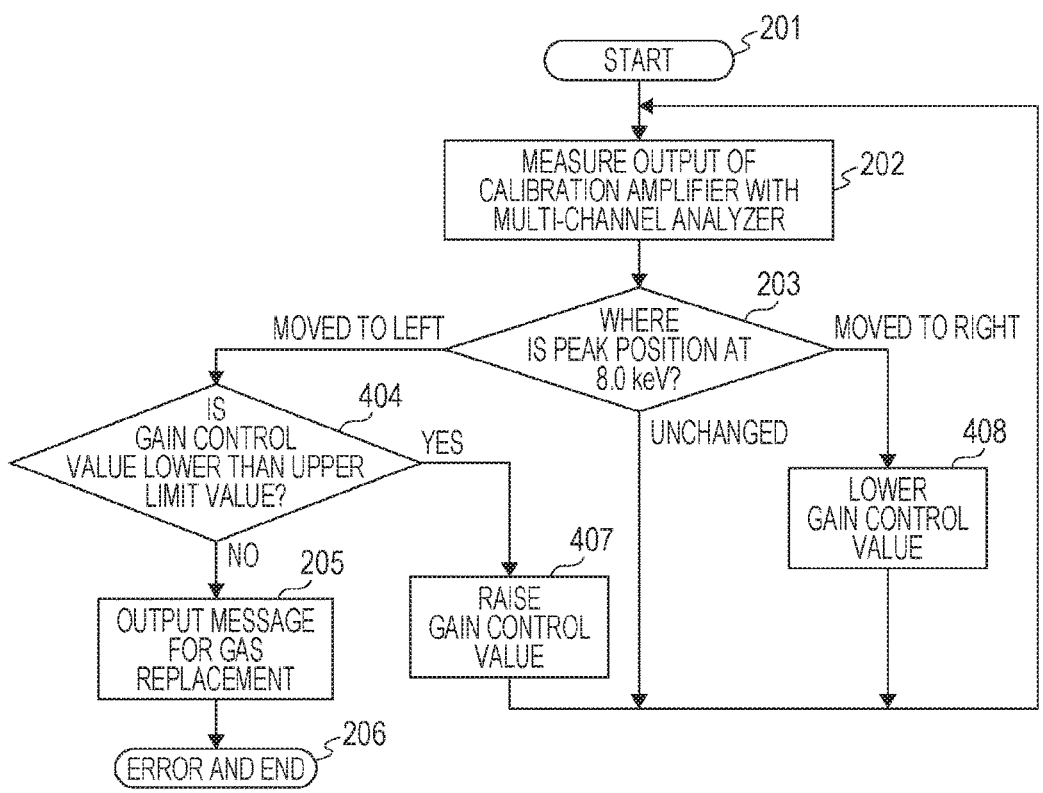
FIG. 4 is a flowchart for describing an operation of the ionizing radiation detection apparatus according to an exemplary embodiment of the disclosure.

FIG. 4 is a flowchart illustrating a method of calibrating the gain according to the present exemplary embodiment. This method is the same as the method according to the first exemplary embodiment illustrated in FIG. 2 except in that the voltage control of the second high-voltage power source is replaced with the control of the gain control value.

In the first exemplary embodiment, the gas electron multiplication factor of the secondary electrons 106 in the secondary electron detection unit 108 is adjusted (controlled) on the basis of the result of detecting the secondary electrons 121 generated as the reference X-ray 120 is photoelectrically absorbed. In contrast, in the present exemplary embodiment, the gain of the measurement amplifier 123 is adjusted (controlled) on the basis of the result of detecting the secondary electrons 121 generated as the reference X-ray 120 is photoelectrically absorbed.

The present disclosure is not limited to these exemplary embodiments, and the information on the energy of the recoil electrons 105 sent from the measurement amplifier 123 to the data processing unit 124 may be numerically adjusted (corrected) on the basis of the result of detecting the secondary electrons 121 generated as the reference X-ray 120 is photoelectrically absorbed. For example, in the data processing unit 124, a conversion factor to be used to calculate the actual energy from the information on the energy can also be corrected. In this case as well, the total gain across the entire process of calculating the energy of the recoil electrons 105 from the generation of the secondary electrons 106 can be kept constant over time.

It is to be noted that the fluorescent X-ray generation plate 113 may be formed of a plurality of fluorescent X-ray generation materials, such as copper and molybdenum. In this case, the conversion factor to be used to calculate the energy can be obtained with higher accuracy through the use of the information on a plurality of energy peak positions obtained from a plurality of reference X-rays 120 of discrete energies.

By controlling the gas electron multiplication gain or the electrical amplification gain as appropriate, a decrease over time in the accuracy of determining the position (direction) of the incident γ-ray can be prevented.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2015-102820 filed May 20, 2015, which is hereby incorporated by reference herein in its entirety.

What is claimed is:

1. An ionizing radiation detection apparatus, comprising:
a chamber holding a scattering gas inside;
a first drift electrode disposed inside the chamber;
a first detection unit disposed inside the chamber so as to oppose the first drift electrode, the first detection unit being configured to detect a first ionization electron produced through Compton scattering caused by an incident γ-ray inside the scattering gas;
a second drift electrode configured to emit a reference X-ray upon being excited by the incident γ-ray;
a second detection unit disposed so as to oppose the second drift electrode, the second detection unit being configured to detect a second ionization electron produced as the reference X-ray is photoelectrically absorbed by the scattering gas; and
a control unit configured to compensate for a change in an amplification factor of a signal output from each of the first detection unit and the second detection unit.

2. The ionizing radiation detection apparatus according to claim 1, wherein the control unit controls a gas electron multiplication factor of each of the first detection unit and the second detection unit.

3. The ionizing radiation detection apparatus according to claim 1, wherein the control unit controls an amplification factor of each of a first amplification unit and a second amplification unit that amplify signals output from the first detection unit and the second detection unit, respectively.

4. The ionizing radiation detection apparatus according to claim 1, wherein the second drift electrode is made of a material containing an element having an atomic number of no less than 22 and no greater than 51.

5. The ionizing radiation detection apparatus according to claim 4, wherein the first drift electrode is made of a material containing an element having an atomic number of no less than 4 and no greater than 21.

6. The ionizing radiation detection apparatus according to claim 4, wherein the second drift electrode contains a plurality of elements.

7. The ionizing radiation detection apparatus according to claim 1, wherein the second drift electrode is disposed so as to surround the first drift electrode.

8. The ionizing radiation detection apparatus according to claim 1, further comprising:
an image display unit; and
a γ-ray detection unit, wherein an intensity distribution of the incident γ-ray is turned into an image on the basis of an output of the first detection unit and an output of the γ-ray detection unit, and the image is displayed on the image display unit.

\* \* \* \* \*